Figure 3:
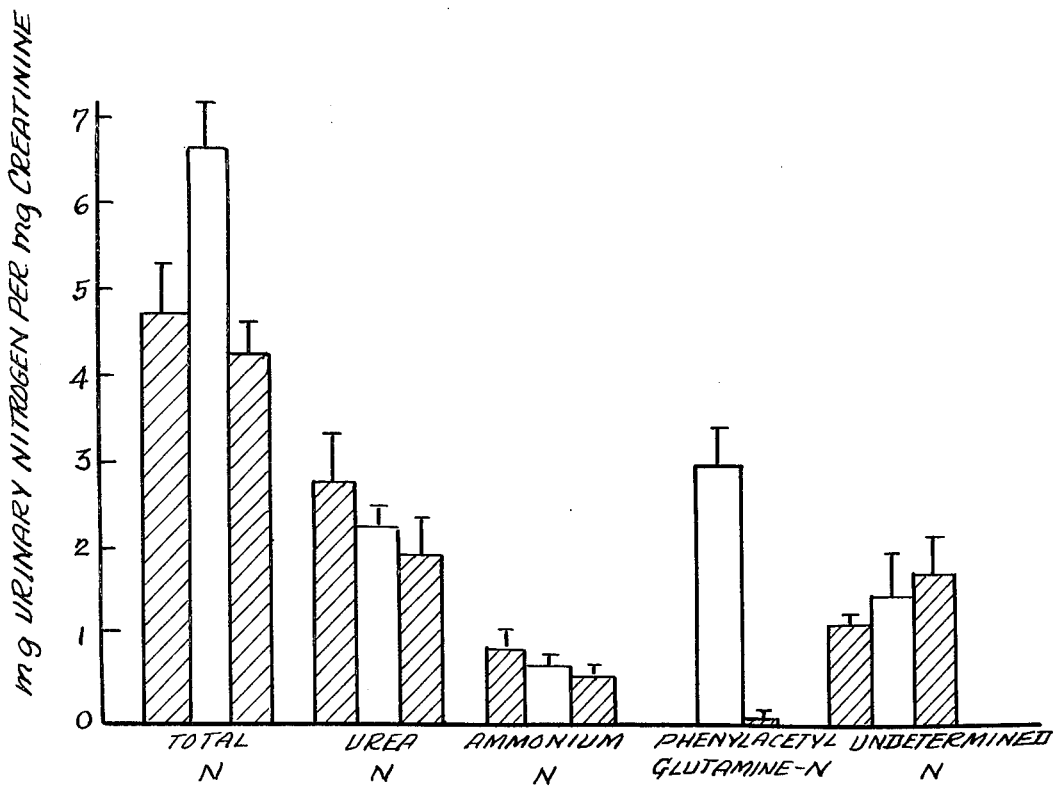

United States Patent [19]

Brusilow et al.

[11] 4,284,647

[45] Aug. 18, 1981

[54] PROCESS FOR WASTE NITROGEN REMOVAL

[75] Inventors: Saul W. Brusilow, Baltimore; Mark L. Batshaw, Pikesville, both of Md.; Norman S. Radin, Ann Arbor, Mich.

[73] Assignee: The Johns Hopkins University, Baltimore, Md.

[21] Appl. No.: 135,685

[22] Filed: Mar. 31, 1980

[51] Int. Cl.$^3$ .............................................. A61K 31/19
[52] U.S. Cl. ..................................................... 424/317
[58] Field of Search ........................................ 424/317

[56] References Cited

PUBLICATIONS

C.A. 8: 3329$^2$ (1914).
C.A. 8: 362$^2$ (1914).
C.A. 16: 2165$^6$ (1922).
C.A. 77: 84783$^h$ (1972).
Sherwin et al., J. Biol. Chem., (1919), 40: 259-263.
James et al., Proc. Royal Soc. London, B, 182: 25-35, (1972).
McCollum et al., J. Biol. Chem., (1913-14) 16: 295-315; 321-325.
Ziter et al., Pediat. Res., 2: 250-253, (1968).
Shih, "The Metabolic Basis of Inherited Diseases", pp. 362-386, McGraw-Hill, (1978).
Sherlock, "Diseases of the Liver and Biliary Systems", 5th ed., pp. 84-106, Blackwell, Oxford, (1975).
Walser, "The Kidney", vol. 2, pp. 1613-1642, W. B. Saunders, (1976).
Close, N. Eng. J. Med. 290, pp. 663-667, (1974).
Lewis, J. Biol. Chem. 18: 225-231, (1914).
Batshaw et al., N. Eng. J. Med., 292: 1085-1090 (1975).
Batshaw et al., Pediat. Res., 12: 221-224, (1978).
Ijpma et al., Clin. Chem., 24/3: 489-492, (1978).
Chaney et al., Clin. Chem., 8: 130-132, (1962).
Fleck, et al., Clin. Chimica Acta., 11: 2-12, (1965).
LaDu et al., "Fundamentals of Drug Metabolism and Drug Disposition", Williams & Williams, (1971), pp. 149-186.

*Primary Examiner*—Frank Cacciapaglia, Jr.
*Attorney, Agent, or Firm*—Cushman, Darby & Cushman

[57] ABSTRACT

A process for controlling waste nitrogen accumulation diseases in humans which comprises administering an effective amount of at least one compound selected from the group consisting of benzoic acid, phenylacetic acid and the non-toxic, pharmaceutically-acceptable salts of the acids to a human suffering from waste nitrogen accumulation.

9 Claims, 8 Drawing Figures

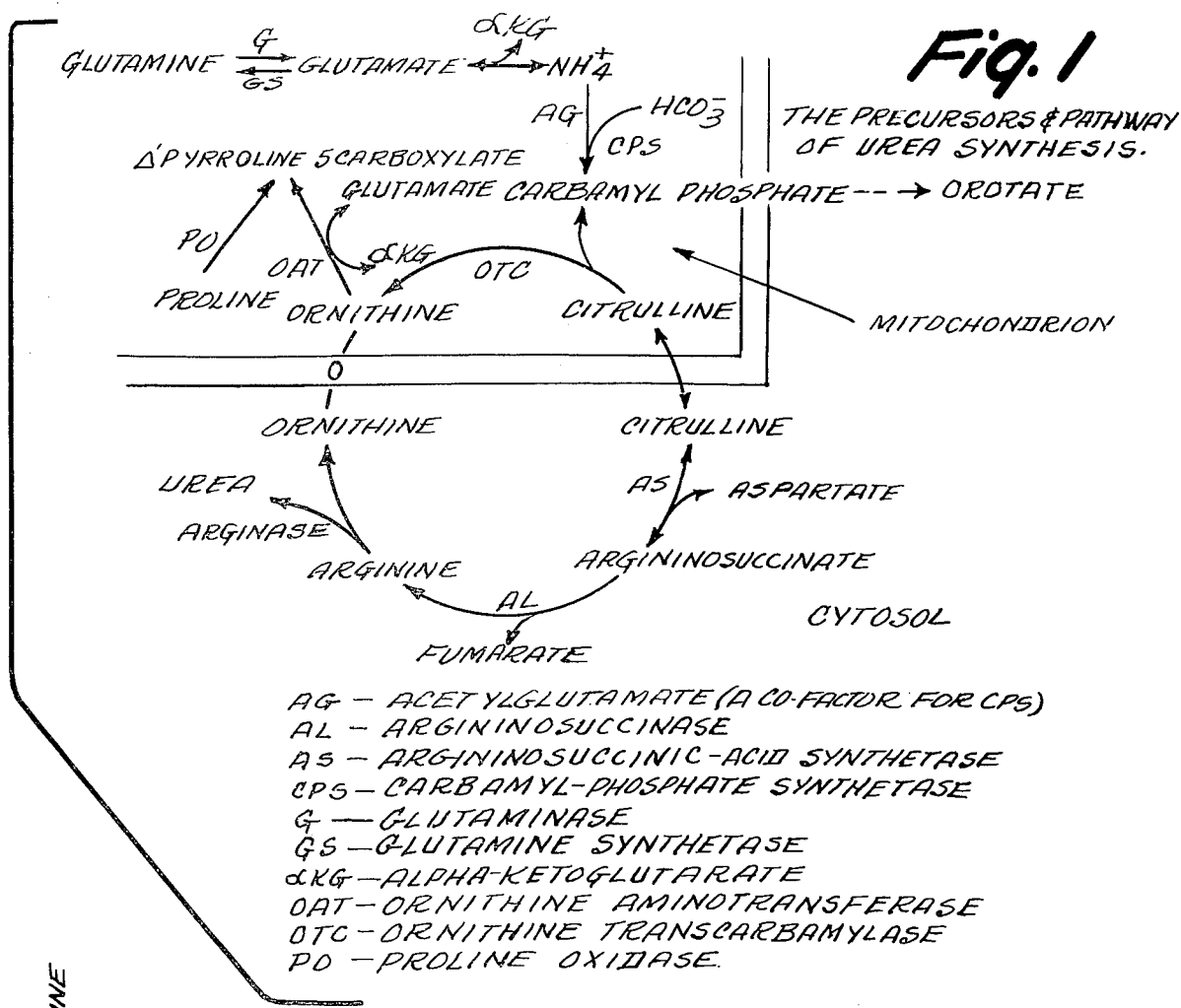
Fig. 1 THE PRECURSORS & PATHWAY OF UREA SYNTHESIS.
AG — ACETYLGLUTAMATE (A CO-FACTOR FOR CPS)
AL — ARGININOSUCCINASE
AS — ARGININOSUCCINIC-ACID SYNTHETASE
CPS — CARBAMYL-PHOSPHATE SYNTHETASE
G — GLUTAMINASE
GS — GLUTAMINE SYNTHETASE
αKG — ALPHA-KETOGLUTARATE
OAT — ORNITHINE AMINOTRANSFERASE
OTC — ORNITHINE TRANSCARBAMYLASE
PO — PROLINE OXIDASE.
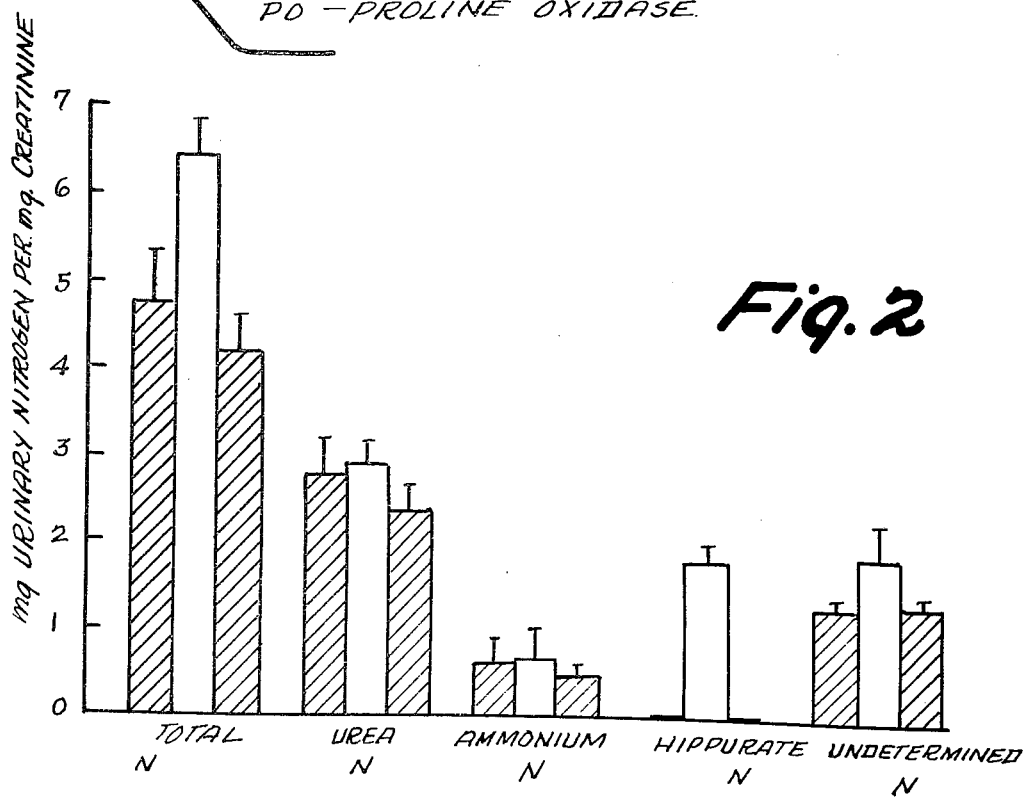
Fig. 2

PROCESS FOR WASTE NITROGEN REMOVAL

The invention described herein was made in the course of work under a grant or award from the Department of Health and Human Services.

The present invention relates to a process for treating humans who suffer from waste nitrogen accumulation in the body.

When the human body is functioning normally, waste nitrogen is effectively excreted, primarily in the form of urinary urea. However, in certain abnormal situations, e.g. in the event of kidney or liver failure or inborn errors of urea synthesis, waste nitrogen will accumulate in the body unless positive steps are taken to avoid this.

In the case of a urea-cycle enzyme defect, the major metabolic abnormality is the inability of the body to convert waste nitrogen into urea. As a consequence, various nitrogenous metabolites accumulate in the body, the most toxic being ammonium although other materials such as glutamine, glutamate and alanine, are usually also present.

Previous therapeutic approaches for treating patients with urea-cycle enzymopathies (as well as other nitrogen accumulation diseases) have been designed to reduce the requirements for urea synthesis by quantitative and qualitative manipulation of dietary protein, amino acids and/or their nitrogen-free analogues. Generally speaking, however, the mortality and morbidity of inborn errors of the urea-cycle remain high and success has been measured more in terms of increased survival time than in the elimination of the undesired effects. Thus, for example, even with the above cited therapeutic approaches, it does not appear that children with the neonatal form of these diseases who survive past one year of age, can normally do so without recurrent episodes of hyperammonemic coma or mental retardation.

The present invention proposes to deal with the problem of waste nitrogen accumulation caused by urea cycle enzyme deficiencies, or other abnormalities in body function (e.g. renal or hepatic failure) which cause such accumulation, by providing an alternative pathway to urea synthesis involving the formation of nitrogen-containing metabolites other than urea which can be readily excreted from the body as urinary nitrogen. To this end, the invention contemplates converting the waste nitrogen into certain amino acid acylation products for urinary discharge from the body. This is accomplished, according to the invention, by administering an effective amount of benzoic acid, phenylacetic acid and/or the non-toxic, pharmaceutically-acceptable salts of these acids, preferably the sodium salts, to one suffering from, or subject to, waste nitrogen accumulation. The benzoic acid or salt thereof converts waste nitrogen in the body to hippuric acid, an amino acid acylation product, which is readily and effectively excreted from the body as urinary nitrogen. Likewise the phenylacetic acid, or salt thereof, causes the formation of phenylacetylglutamine, an amino acid acetylation product which is also easily and quickly excreted as urinary nitrogen. The invention thus effectively by-passes urea synthesis while providing a ready way of excreting waste nitrogen from the body.

Benzoic acid or phenylacetic acid, or salts thereof, may be used separately or as mixtures of the acids and/or salts. The amount of acid and/or salt administered for present purposes will vary rather widely from case to case. Normally, however, the daily dosage of acid and/or salt utilized will fall in the range of 100–400 mg/kg body weight for children and from 7.5 to 15 grams for adults. Generally speaking, the size and frequency of the dosages given at any time can be varied as desired provided the indicated total daily dose is not significantly modified. The administration may be carried out intravenously or orally (e.g. in the form of sterile injectable solutions, pills, tablets, capsules, solutions, suspensions or the like).

It has previously been disclosed that benzoic acid or phenylacetic acid as such, or as salts thereof, form hippuric acid and phenylacetylglutamine, which can be discharged from the body as urinary nitrogen. Thus, it is known from studies by Lewis (J. Biol. Chem. 18, 225–231 (1914)) that benzoic acid or sodium benzoate, when orally administered to a healthy man, is eliminated rapidly as urinary hippuric acid. According to Lewis, the urinary hippurate nitrogen replaces the urinary urea nitrogen so that there is little change in total urinary nitrogen excretion.

The Lewis publication, as well as other publications on benzoate or phenylacetate metabolism[1] are concerned with the ability of the body to detoxify benzoic acid, phenylacetic acid or their sodium salts and thus eliminate benzoate or phenylacetate from the body. There is no disclosure in these prior publications of the present concept of using benzoic acid, phenylacetic acid or their salts to convert toxic waste nitrogen to urinary hippuric acid or phenylacetylglutamine in order to remove waste nitrogen from the body as an alternative, or adjunct, to urea synthesis with subsequent urinary excretion.

[1] LaDu, B. N., Mandel, H. G., Way, E. L. Fundamentals of Drug Metabolism and Drug Disposition, Williams & Wilkins 1971.

It is also noted that Shiple and Sherwin (J. Am. Chem. Soc. 44: 618–624, 1922) have disclosed that the oral administration of benzoic acid and phenylacetic acid results in the formation and excretion of urinary hippuric acid and phenylacetylglutamine, respectively. The hippuric acid or phenylacetylglutamine is formed at the expense of urinary urea. The authors indicate that following both benzoate and phenylacetic acid administration, the partition of urinary nitrogen was dramatically altered so that urea nitrogen accounted for as little as 12% of urinary nitrogen and hippurate and phenylacetylglutamine nitrogen accounted for as much as 60% of urinary nitrogen.

Shiple and Sherwin, like Lewis, are concerned with the detoxification of benzoic acid and phenylacetic acid (or salts thereof) when administered to humans rather than being concerned with the use of these materials to detoxify waste nitrogen accumulating in the body.

Other publications describing the conversion of phenylacetic acid to phenylacetylglutamine when the acid is administered to humans include Ambrose et al "Further Studies on the Detoxification of Phenylacetic Acid", J. Biol. Chem. 1933; 101: 669–675; and James et al "The Conjugation of Phenylacetic Acid in Man, Sub-Human Primates and Some Non-Primate Species", Proc. R. Soc. Lond. B, 1972; 182: 25–35. Of these publications, Ambrose et al reported that they found 98% of orally administered phenylacetic acid (5–7 g/day for 3 months in man) was excreted in the urine as phenylacetylglutamine while James et al disclose that they gave 85 mg/kg of phenylacetic acid to a man and found that 91% of this dose was excreted in the urine as phenylacetylglutamine. No adverse effects are noted in these studies although an earlier paper (Sherwin et al, J. Biol.

Chem. 1919; 40: 250–263) reported thirst, nausea, and dizziness after a single dose of phenylacetic acid.

The conjugation of benzoic acid with glycine to form hippuric acid involves two reactions catalyzed by the mitochondrial-matrix enzymes, benzoyl thiokinase and a glycine-specific transacylase. Lewis's studies showed that this pathway can convert 10 g sodium benzoate to hippuric acid in less than 24 h in the adult male. Hippuric acid is well suited for renal excretion because its renal clearance is five times the glomerular filtration rate.

It will be appreciated from the foregoing that benzoic acid and sodium benzoate can be used interchangeably. Sodium benzoate, like the acid, is non-toxic (except perhaps in neonatal hyperbilirubinaemia, where in vitro experiments suggest that it competes for bilirubin-binding sites on albumin) and has been used to treat infants with non-ketotic hyperglycinaemia (Ziter et al, Pediat. Res. 2: 250–253, 1968).

The synthesis of phenylacetylglutamine using phenylacetic acid also involves a two-stage reaction which, in this case, includes acetylation of glutamine to form the desired phenylacetylglutamine, the latter, like hippuric acid, being rapidly excreted by the kidney. Acetylation and excretion of glutamine rather than glycine has three advantages: (i) glutamine contains two nitrogen atoms per molecule, (ii) it accumulates in urea-cycle enzymopathies, and (iii) it is in equilibrium with glutamate, the nitrogen donor for urea synthesis.

The accompanying drawings serve to further illustrate the invention. Of these, FIG. 1 diagrammatically shows the pathways of urea synthesis, including the known points of genetic defects. In all these disorders nitrogen accumulates, usually in the form of ammonium, glutamine, glutamate, and alanine. Furthermore, each defect is characterized by the accumulation of the specific substrate for the deficient enzyme which may be carbamyl phosphate (manifested by accumulation of orotic acid), citrulline, argininosuccinic acid, and arginine. It will be appreciated that the purpose of the invention is to provide an alternative to the indicated urea synthesis for excretion of urinary nitrogen.

FIGS. 2-8 graphically illustrate various results obtained by using the invention as discussed in more detail hereinafter.

The invention is also illustrated by the following:

EXAMPLE I

Patients with urea-cycle enzymopathies were studied to determine the effect of sodium benzoate or phenylacetic acid on urinary nitrogen excretion and to determine the effectiveness of sodium benzoate on plasma ammonium levels in patients in hyperammonemic coma.

Urinary nitrogen excretion was studied in a clinically stable 17-year old, 40 kg female, with carbamyl phosphate synthetase (CPS) deficiency who was maintained on a diet containing 27 g of protein and 1800 calories while the following protocols were followed. Sodium benzoate (6.25 g/d) or phenylacetic acid (6.4 g/d) was administered orally for 11 and 8 days, respectively. Each experimental period was preceded and followed by a control period totalling 8-10 days. Daily incomplete twenty-four hour urine collections (the patient was episodically incontinent) were made. Urinary urea nitrogen, ammonium nitrogen, and creatinine were measured by standard techniques. Hippurate and phenylacetylglutamine were measured by reverse phase liquid chromatography using a Waters $C^{18}$ column with a 20% methanol solution of 0.01 M acetate buffer, pH 3, as an eluant. Total urinary nitrogen was measured after Kjeldahl digestion[1] of 0.1 ml urine following which 0.1 ml aliquots of the digestion mixture (diluted to 30 ml) were analyzed for ammonium by the indophenol reaction[2]. Plasma glycine was measured by automated ion-exchange chromatography. Plasma glutamine, glutamate and alanine were measured by fluorometric enzymatic techniques[3] and plasma ammonium was measured either on venous plasma by the Dupont ACA[4] or on capillary plasma by a cation exchange method[5].

[1] A. Fleck and H. N. Munro, Clin. Chim. Acta. 11, 2 (1965).
[2] A. L. Chaney and E. P. Marbach, Clin. Chem. 8, 130 (1962).
[3] M. Batshaw and S. Brusilow, Pediat. Res. 12, 221 (1978).
[4] S. T. Ijpma, B. G. Blijenberg, B. Leijnse, Clin. Chem. 24,489.
[5] M. Batshaw, S. Brusilow, M. Walser, New Engl. J. Med. 292, 1085 (1975).

FIG. 2 compares the amount and partition of urinary nitrogen during the control and sodium benzoate administration periods. The partition of urinary nitrogen (mg nitrogen per mg creatinine±SEM) of the patient while receiving sodium benzoate is shown in shaded bars compared to a control period (open bars). There was a 58% increase in total urinary nitrogen excretion while the patient was receiving sodium benzoate as compared to the control period. Urinary hippurate nitrogen accounted for this increase in urinary nitrogen excretion. The plasma concentrations of several urea precursors during the control (n=6) and experimental periods (n=8) were respectively ($\mu$M+SEM): ammonium, 29.5±1.0 vs 22.9±2.2, p<0.02; glutamine, 1675±49 vs 1422±109, alanine, 952±107 vs 901±91; glutamate, 36±5.3 vs 27±4.2. The plasma glycine levels during the control (n=4) and experimental periods (n=6) were similar 247±8 vs 294±49.

The effect of phenylacetic acid administration on amount and partition of urinary nitrogen is shown in FIG. 3. The partition of urinary nitrogen (mg nitrogen per mg creatinine±SEM) of the patient while receiving phenylacetic acid is shown in shaded bars and compared with a control period (open bars). There was a 49% increase in total urinary nitrogen while the patient was receiving phenylacetic acid as compared to the control period. Urinary phenylacetylglutamine nitrogen accounted for this increase in urinary nitrogen excretion. The mean plasma concentrations ($\mu$M) or urea precursors during the control (n=4) and experimental periods (n=3) were respectively: ammonium, 29.3 vs 17.7; glutamine, 1753 vs 1533; glutamate, 51.5 vs 26.3; alanine, 646 vs 670.

The foregoing results indicate that acetylation of glycine by benzoic acid and acetylation of glutamine by phenylacetic acid with subsequent renal excretion of the respective products, hippuric acid and phenylacetylglutamine, are quantitatively significant alternative mechanisms of waste nitrogen disposal in patients with inborn defects of urea synthesis.

Both mechanisms require adequate amounts of the natural precursors of the conjugate, i.e. glycine or glutamine. While the patient received benzoate for 11 days there was a significant decrease in the plasma ammonium level. The plasma glycine level was unchanged indicating that de novo glycine synthesis was, in this case, sufficient for hippurate synthesis. During therepy with phenylacetic acid there were apparent decreases in the plasma concentrations of ammonium and glutamine although the small number of such determinations preclude statistical evaluation.

Figure 4:
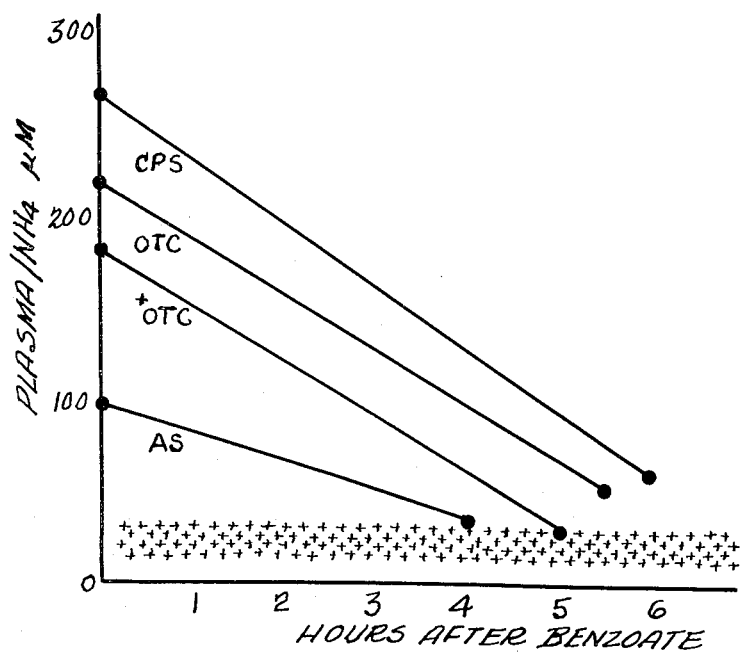

The foregoing observations indicate that benzoate administration can be used in acutely reducing plasma ammonium levels during hyperammonemic episodes. Accordingly, four patients were given a single dose (orally or intravenously) of sodium benzoate (250–350 mg/kg) during such a hyperammonemic episode. The effect of the sodium benzoate on plasma ammonium levels in the patients in hyperammonemic coma is shown in FIG. 4, the patients being: CPS, an 18-year old female with partial carbamyl phosphate synthetase deficiency given 250 mg/kg orally; OTC, a 6-year old female with partial ornithine transcarbamylase deficiency given 250 mg/kg orally; and OTC, an 11-month old male with ornithine transcarbamylase deficiency given 350 mg/kg intravenously and AS, an 11-month old female with argininosuccinic acid synthetase deficiency given 300 mg/kg orally. The hatched area in FIG. 4 denotes normal plasma levels of ammonium (17–33$\mu$M).

In each case there was a prompt fall in the plasma ammonium level and clinical improvement following administration of sodium benzoate. This change is believed to be a consequence of the incorporation of ammonium or glutamate in the de novo synthesis of glycine by one of three pathways; from ammonium via the glycine cleavage complex, from glutamate via glyoxylate transamination or via de novo serine synthesis.

Figure 5:
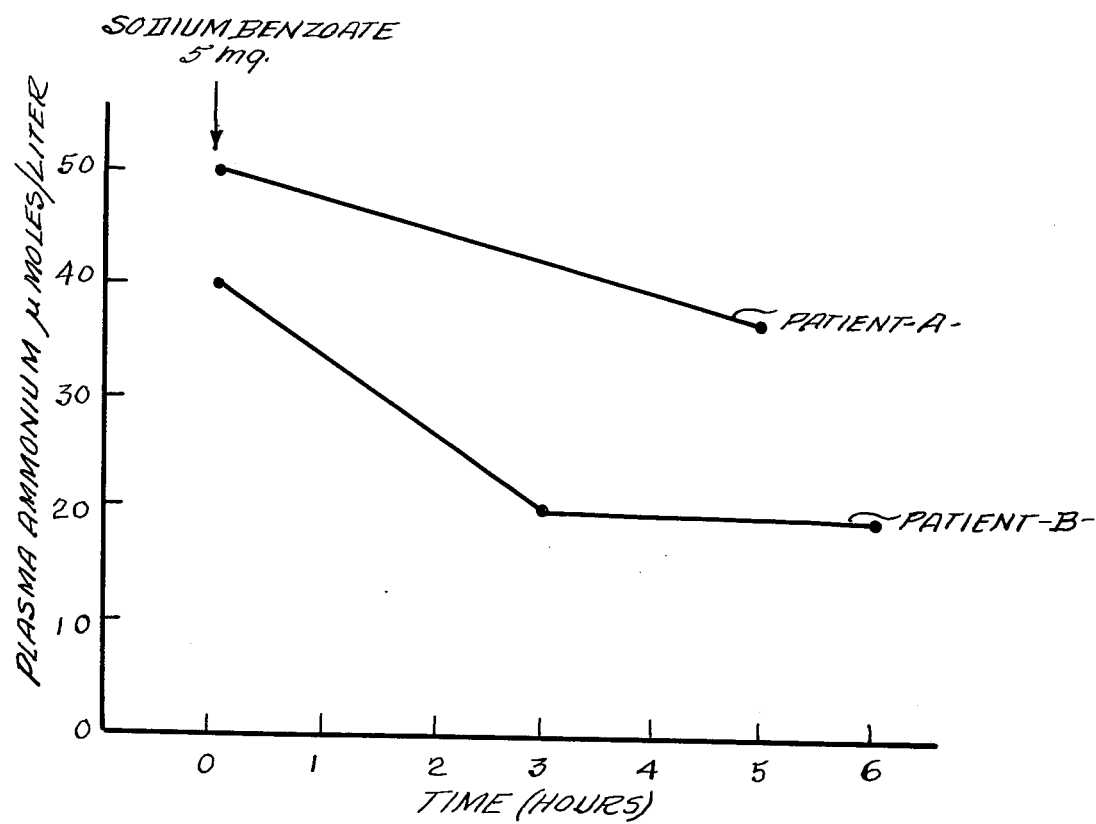

FIG. 5 shows the course of plasma ammonium level in two adults with stable chronic liver disease who were each given 5 grams of sodium benzoate. The plasma ammonium level in $\mu$moles per liter is plotted against time (hours) after the administration of 5 grams sodium benzoate. The results show in one case (patient A) a gradual dropping of the plasma ammonium level after administration while in the other (patient B), the plasma ammonium leveled off after a relatively sharp drop for up to three hours after administration. In both cases, the results indicated effective control of the plasma ammonium level using sodium benzoate.

Figure 6:
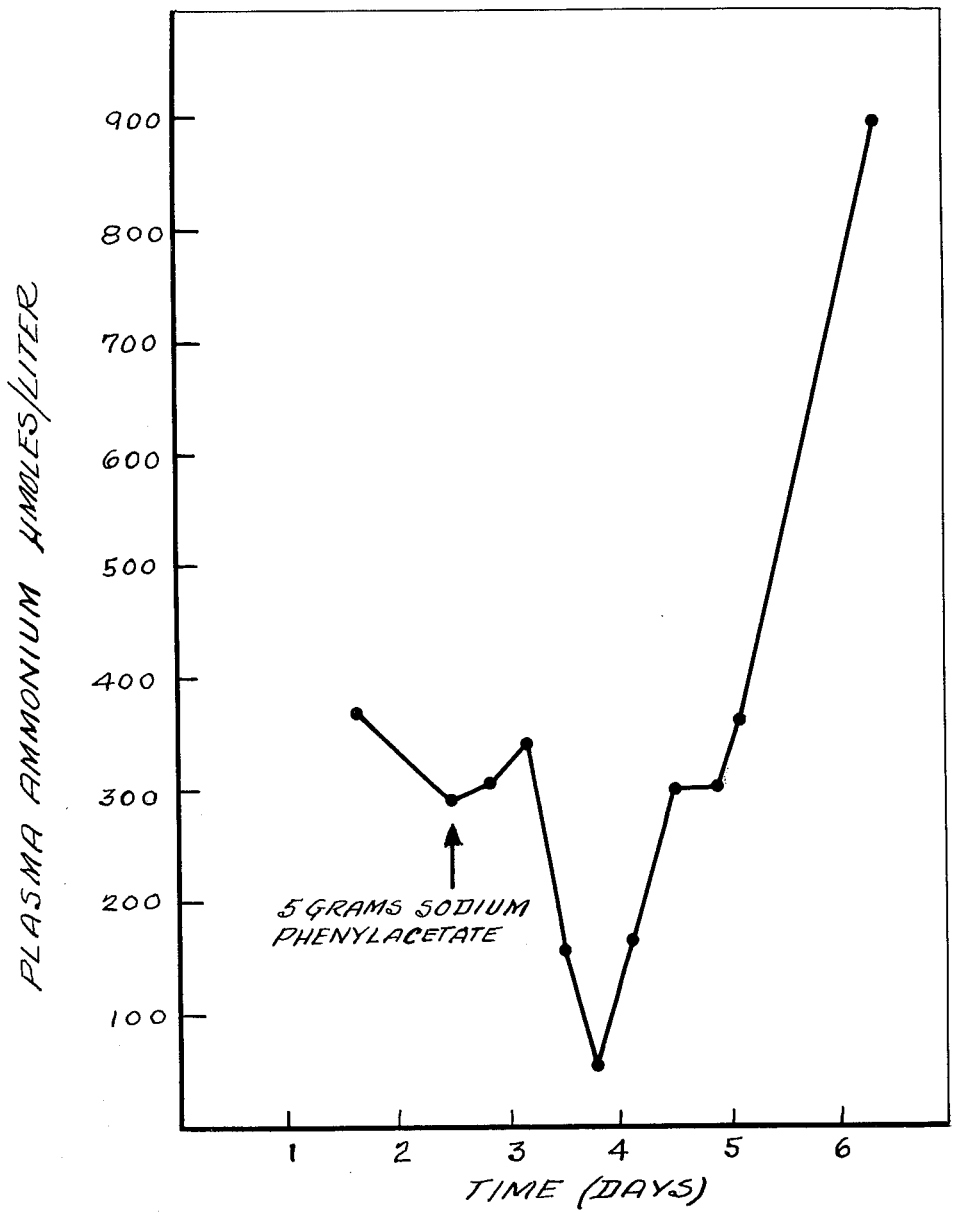

FIG. 6 graphically shows the course of the plasma ammonium level in a 4-year old male child with terminal hepatic coma. The child was given 5 grams of sodium phenylacetate at about mid-day of day 2. As shown, the plasma ammonium level, which was at about 300$\mu$ mols per liter, rose immediately after administration of the sodium phenylacetate but then dropped sharply over the course of the next day to about 50$\mu$ mols. While the effect of the 5 grams phenylacetate administration was not long-lasting, as evidenced by the subsequent increase in the plasma ammonium level over the next several days to the point where the patient died, the reduction of the plasma ammonium level on administration of the sodium phenylacetate is an indication that such administration would be effective in the treatment of hepatic coma.

Figure 7:
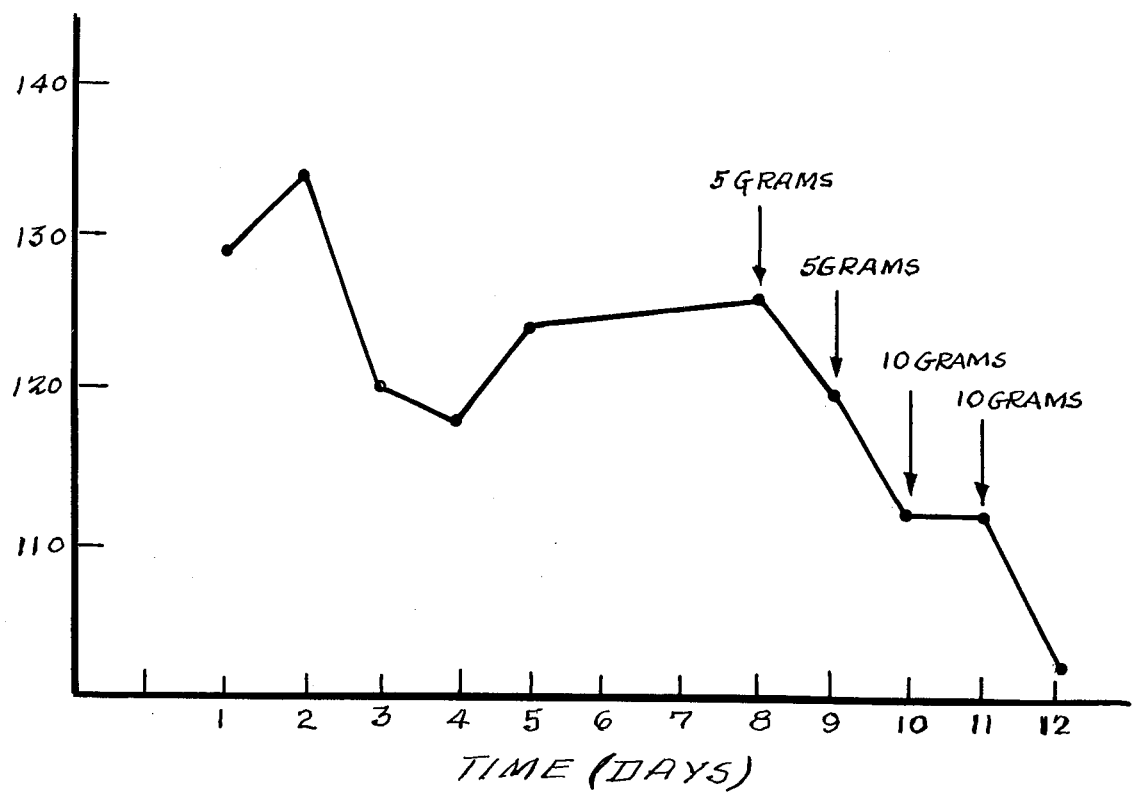

FIG. 7 shows the course of the serum urea nitrogen of an adult woman who was given 5 grams of sodium benzoate on days 8 and 9 and 10 grams of sodium benzoate on days 10 and 11. As shown, the amount of the serum urea nitrogen (measured in milligrams per 100 milliliters) was substantively reduced on administration of the benzoate.

The data shown graphically in FIGS. 5–7 indicate that sodium benzoate and phenylacetate would be useful in treating hyperammonemia in liver failure and that sodium benzoate would be useful in treating uremia. It is noted that in the case of uremia the serum urea nitrogen level is the most useful guide as to the state of nitrogen accumulation whereas the ammonium level is the most useful indicator in liver disease or urea cycle enzymopathies.

Figure 8:
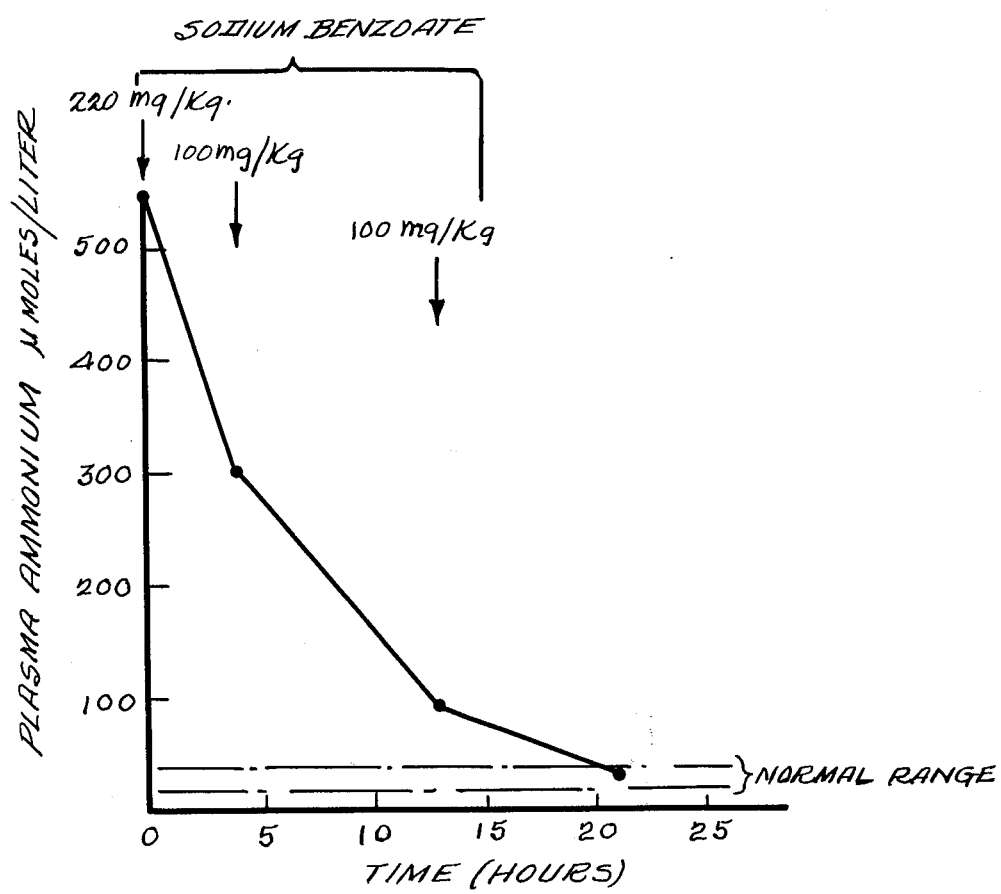

The possible application of the present invention in the treatment of Reye's syndrome is shown by FIG. 8. This figure illustrates the course of the plasma ammonium level in a 4-year old girl with Reye's syndrome who was treated with three doses of sodium benzoate orally. The doses were 220 mg/kg, 100 mg/kg and 100 mg/kg at the intervals shown. As indicated, the benzoate markedly reduced the plasma ammonium level in less than a day's time from about 550$\mu$ mols per liter to below 40$\mu$ mols per liter, i.e. into the normal range.

It will be appreciated from the foregoing that the administration of benzoic acid and/or phenylacetic acid, as such, or in salt form, to form their respective amino acid acetylation products (hippuric acid and phenylacetylglutamine) for urinary nitrogen discharge, according to the invention, is of general application against diseases and malfunctions involving waste nitrogen accumulation in the body, e.g. urea-cycle enzymopathies, portal-systemic encephalopathy, Reye's syndrome, and uraemia.

Having described the invention, what is claimed is:

1. A process for controlling waste nitrogen accumulation diseases in humans, caused by an impairment in the normal synthesis of urea from ordinary waste nitrogen in the body or in the normal excretion thereof, said process comprising administering an effective amount of at least one compound selected from the group consisting of benzoic acid, phenylacetic acid and the non-toxic, pharmaceutically-acceptable salts of said acids to a human suffering from such waste nitrogen accumulation disease, the amount of said compound used being sufficient to react with the waste nitrogen to form an amino acid acylation product for urinary discharge of said product.

2. The process of claim 1 wherein a mixture of benzoic acid and phenylacetic acid, or salts thereof, is administered.

3. The process of claim 1 wherein the administration is continued until the accumulated waste nitrogen is discharged as urinary nitrogen.

4. The process of claim 1 wherein the human is one with a urea-cycle enzymopathy.

5. The process of claim 1 wherein the human is one suffering from uremia.

6. The process of claim 1 wherein the human is one suffering from a hepatic disorder.

7. The process of claim 1 wherein the human is one suffering from Reye's syndrome.

8. The process of claim 1 wherein the administration of the benzoic acid or phenylacetic acid, or salts thereof, synthesizes hippuric acid and phenylacetylglutamine, respectively, and the synthesized product is discharged as urinary nitrogen.

9. The process of claim 1 wherein the salt is sodium salt.

* * * * *